US009131913B2

(12) United States Patent
Sehnert et al.

(10) Patent No.: US 9,131,913 B2
(45) Date of Patent: Sep. 15, 2015

(54) REGION-SELECTIVE FLUOROSCOPIC IMAGE COMPRESSION

(75) Inventors: William J. Sehnert, Fairport, NY (US); David H. Foos, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 302 days.

(21) Appl. No.: 13/523,264

(22) Filed: Jun. 14, 2012

(65) Prior Publication Data

US 2013/0336552 A1    Dec. 19, 2013

(51) Int. Cl.
G06K 9/00 (2006.01)
A61B 6/00 (2006.01)
G06F 19/00 (2011.01)
A61B 19/00 (2006.01)

(52) U.S. Cl.
CPC .............. *A61B 6/487* (2013.01); *A61B 6/469* (2013.01); *G06F 19/321* (2013.01); *A61B 6/463* (2013.01); *A61B 6/563* (2013.01); *A61B 2019/5238* (2013.01)

(58) Field of Classification Search
CPC ............................................... H04N 19/00248
See application file for complete search history.

(56) References Cited

U.S. PATENT DOCUMENTS

| 5,954,650 | A | * | 9/1999 | Saito et al. | 600/425 |
| 6,298,173 | B1 | | 10/2001 | Lopresti | |
| 6,477,201 | B1 | * | 11/2002 | Wine et al. | 375/240.08 |
| 6,937,767 | B1 | | 8/2005 | Burak et al. | |
| 6,970,585 | B1 | * | 11/2005 | Dafni et al. | 382/131 |
| 7,929,793 | B2 | | 4/2011 | Gering et al. | |
| 8,121,417 | B2 | | 2/2012 | Gering et al. | |
| 2006/0126910 | A1 | * | 6/2006 | Conrad et al. | 382/128 |
| 2008/0232699 | A1 | * | 9/2008 | Gering et al. | 382/232 |
| 2009/0208122 | A1 | * | 8/2009 | Taketa et al. | 382/236 |
| 2009/0304242 | A1 | * | 12/2009 | Omi et al. | 382/128 |
| 2010/0053213 | A1 | * | 3/2010 | Ishida et al. | 345/629 |
| 2011/0025682 | A1 | * | 2/2011 | Keller et al. | 345/418 |
| 2011/0122242 | A1 | * | 5/2011 | Garud et al. | 348/79 |

OTHER PUBLICATIONS

Schwartz, Berkner, Gormish, "Optimal tile boundary artifact removal with CREW", Proc. of Picture Coding Symposium, (1999) pp. 285-288.

* cited by examiner

*Primary Examiner* — Bhavesh Mehta
*Assistant Examiner* — Andrew Moyer

(57) ABSTRACT

A method for displaying a sequence of fluoroscopic images of a subject defines, within the image area of a digital image receiver and in response to one or more viewer instructions, a region of interest and a background region that lies outside the defined region of interest. A succession of fluoroscopic images is obtained from the digital image receiver and, for image pixels within each of the succession of fluoroscopic images, background region pixel data are encoded and transmitted to the display apparatus using a lossy encoding. Region of interest pixel data is transmitted to the display apparatus using a lossless encoding. The succession of fluoroscopic images is displayed.

17 Claims, 14 Drawing Sheets

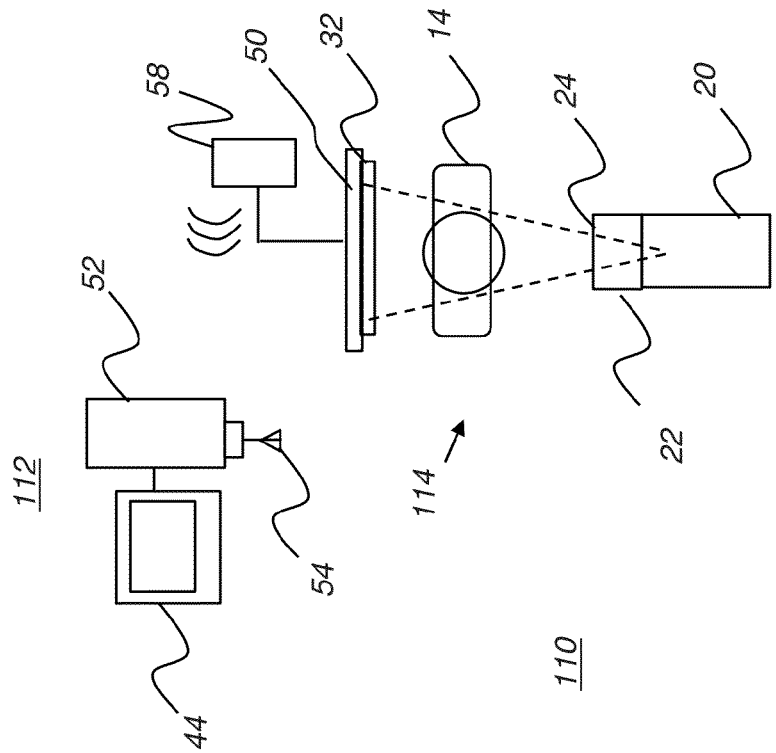
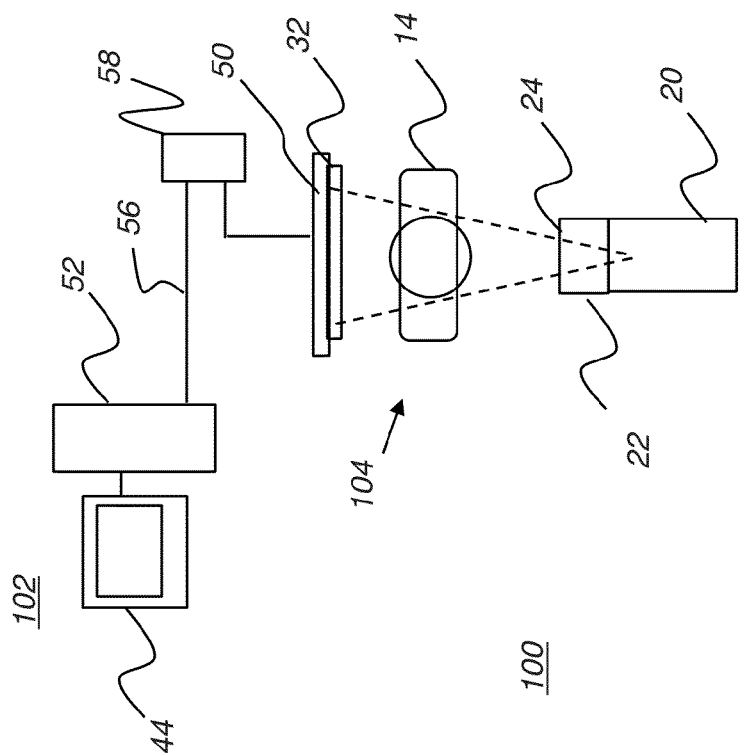
FIG. 2B
FIG. 2A

REGION-SELECTIVE FLUOROSCOPIC IMAGE COMPRESSION

FIELD OF THE INVENTION

The invention relates generally to the field of medical imaging and more particularly to a method for region-selective compression used in fluoroscopic imaging.

BACKGROUND

Fluoroscopy provides near real-time visualization of internal anatomy of a patient, with the ability to monitor dynamic processes, including tracking the relative motion of various types of features such as probes or other devices, fluids, and structures. Fluoroscopy is used, for example to help in diagnosis and to position the patient for subsequent image recording or to position and manipulate various types of devices for interventional procedures.

The block diagram of FIG. 1 shows components in the imaging path of a conventional fluoroscopy system 10 for obtaining images of a patient 14 or other subject. Radiation from an x-ray source 20 that typically uses a collimator 22 and filtration 24 is directed through a patient 14 to an image intensifier 30. Generally a grid 32 is provided. A camera 40 then captures successive video frames from the x-ray exposure and generates images that are displayed on a display monitor 44.

The need to provide near real-time imaging places demands on apparatus and processing in the imaging chain. Because of the low radiation levels used, image intensifier 30 must provide high gain for substantial amplification of the low-level image data. Successive image frames from patient exposures are captured by camera 40 and displayed at video rates, providing the best image contrast and resolution that are possible within the constraints of exposure and capture hardware.

Applicants have noted that there is a need for methods that enable the use of DR and wireless DR receivers for imaging in fluoroscopy systems.

SUMMARY

An object of the present application is to address the need for efficient transfer of image data suitable for fluoroscopy and related near-real-time imaging systems. Methods provided take advantage of the nature and purpose of fluoroscopic examination and are not dependent on particular imaging hardware. Thus, the methods of the present application can be adapted to systems that employ hard-wired data transfer or wireless transfer of image data. Advantageously, by using selectively applied image compression, embodiments of the present application reduce the overall amount of data that must be transferred for each video frame, so that the image processing and display apparatus of the fluoroscopy system can respond to provide near real-time image display.

These objects are given only by way of illustrative example, and such objects may be exemplary of one or more embodiments of the application. Other desirable objectives and advantages inherently achieved by the disclosed application may occur or become apparent to those skilled in the art. The invention is defined by the appended claims.

According to one aspect of the invention, there is provided a method for displaying a sequence of fluoroscopic images of a subject, the method comprising: defining, within the image area of a digital image receiver, in response to one or more viewer instructions, a region of interest and a background region that lies outside the defined region of interest; obtaining a succession of fluoroscopic images at the digital image receiver and, for image pixels within each of the succession of fluoroscopic images: (i) encoding and transmitting background region pixel data to a display apparatus using a lossy encoding; (ii) transmitting region of interest pixel data to the display apparatus using a lossless encoding; and displaying the succession of fluoroscopic images on the display apparatus.

According to an alternate aspect of the present invention, there is provided a method for displaying a sequence of fluoroscopic images of a patient, the method comprising: defining, within the image area of a digital image receiver, in response to one or more viewer instructions, a region of interest and a background region that lies outside the defined region of interest; obtaining a succession of fluoroscopic images at a digital image receiver and, for image pixels within each of the succession of images: (i) encoding and transmitting background region pixels to the display apparatus using a lossy encoding, with transmission at a first refresh rate; (ii) transmitting region of interest pixels to the display apparatus using a second encoding, with transmission at a second refresh rate that is higher than the first refresh rate; and displaying the succession of fluoroscopic images on the display apparatus.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 2A is a schematic block diagram showing components of a fluoroscopic imaging apparatus using wired image data transmission.

FIG. 2B is a schematic block diagram showing components of a fluoroscopic imaging apparatus using wireless image data transmission.

DETAILED DESCRIPTION OF THE EMBODIMENTS

Figure 1:
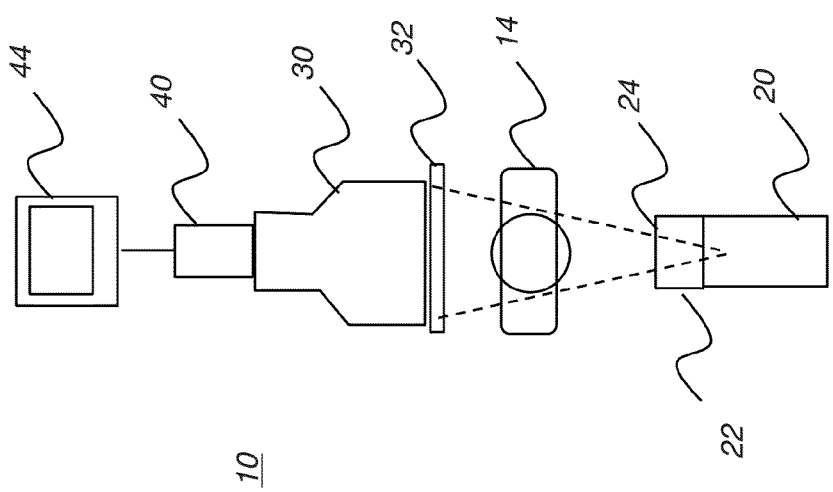
FIG. 1 is a schematic block diagram showing components of a conventional fluoroscopic imaging apparatus.

The following is a detailed description of the preferred embodiments of the invention, reference being made to the drawings in which the same reference numerals identify the same elements of structure in each of the several figures.

Where they are used, the terms "first", "second", and so on, do not necessarily denote any ordinal, sequential, or priority relation, but are simply used to more clearly distinguish one element or set of elements from another, unless specified otherwise. The term "pixel" has its standard meaning, referring to a picture element, expressed as a unit of image data.

In the context of the present disclosure, the terms "viewer", "operator", and "user" are considered to be equivalent and refer to the viewing practitioner or other person who views and manipulates an x-ray image, such as a fluoroscopic image, on a display monitor. A "viewer instruction" can be obtained from explicit commands entered by the viewer or may be implicitly obtained or derived based on some other user action, such as setting up or initiating an exposure or making a collimator adjustment, for example.

In the context of the present invention, the terms "near video rate" and "near real-time" relate to the response time for image data display. For fluoroscopy, because of detector response limitations and because it is beneficial to help reduce radiation levels, what is considered real-time or near-real-time video presentation is generally at a slower frame refresh rate than rates used for conventional video imaging. Thus, in the context of fluoroscopy imaging for example, a useful "near real-time" refresh rate is at least about 1 or more frames per second.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual organ, bone, or structure, or a path from one chamber to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

As digital radiography (DR) imaging receivers improve in image quality and acquisition speed, Applicants anticipate that these devices can be employed not only for conventional radiography imaging, but also for fluoroscopy applications, to eliminate/reduce the need for the dedicated image intensifier hardware used with conventional fluoroscopy systems such as that shown in FIG. 1. To be useful for fluoroscopy, however, image data acquisition and transfer rates are desired to be sufficient for near real-time image data acquisition, including for DR receivers that provide image data using wireless data transfer mechanisms. With high-speed wireless data communications, image data transfer speeds need to have acceptable high-speed data flow rates that are suitable for fluoroscopic use. Applicants have noted that there is a need for methods that enable the use of DR and wireless DR receivers for imaging in fluoroscopy systems.

Embodiments of the present invention enable the use of a digital radiography (DR) receiver as the digital image receiver for receiving radiation in the fluoroscopy system and for generating, processing, and transmitting the received image data, as image pixels (picture elements), to a display apparatus for fluoroscopic display. FIGS. 2A and 2B respectively show two general arrangements of system components for a fluoroscopy system 100 that uses an interconnect cable 56 for image data transmission and a fluoroscopy system 110 that employs wireless transmission of image data.

FIG. 2A shows fluoroscopy system 100 that has a fluoroscopy capture apparatus 104 that includes DR receiver 50 and an image processing unit 58 that obtains and processes the image data from detector 50 and transmits the processed image data to a host processor 52 through an interconnect cable 56 for providing the image data to a fluoroscopy display apparatus 102 that includes a display monitor 44. Host processor 52 is a computer or dedicated workstation or other logic and control processor that obtains the processed fluoroscopy image data and displays the obtained images at near-video rates to the practitioner or other viewer.

FIG. 2B shows fluoroscopy system 110 that has a fluoroscopy capture apparatus 114 in which image processing unit 58 provides the processed image data of a subject to a fluoroscopy display apparatus 112 in wireless form. Host processor 52 has a wireless receiver element 54 for providing the image data to fluoroscopy display apparatus 112 for viewing on display monitor 44.

For both FIG. 2A and FIG. 2B embodiments, image processing unit 58 may be integrated into DR receiver 50 or may be a separate processor apparatus. Image processing unit 58 may be a dedicated microprocessor, host processor, or other type of computer device, including a device that performs logic instructions that have been encoded in hardware.

The difficulty in obtaining processed image data of the subject at near video rates relates to the need for both high-speed data access between DR receiver 50 and image processing unit 58 and high data transmission rates from image processing unit 58 to host processor 52 (FIGS. 2A, 2B). It can be appreciated that this difficulty is more pronounced with the wireless transmission of fluoroscopy system 110 in FIG. 2B, since wireless rates are generally slower than data rates with a hard-wired connection and since wireless transmission can be further hindered by intermittent noise and interference. Thus, methods for compacting the image data as much as possible offer one way to help alleviate the potential data transmission bottleneck that can occur with either wired or wireless transmission.

Figure 3:
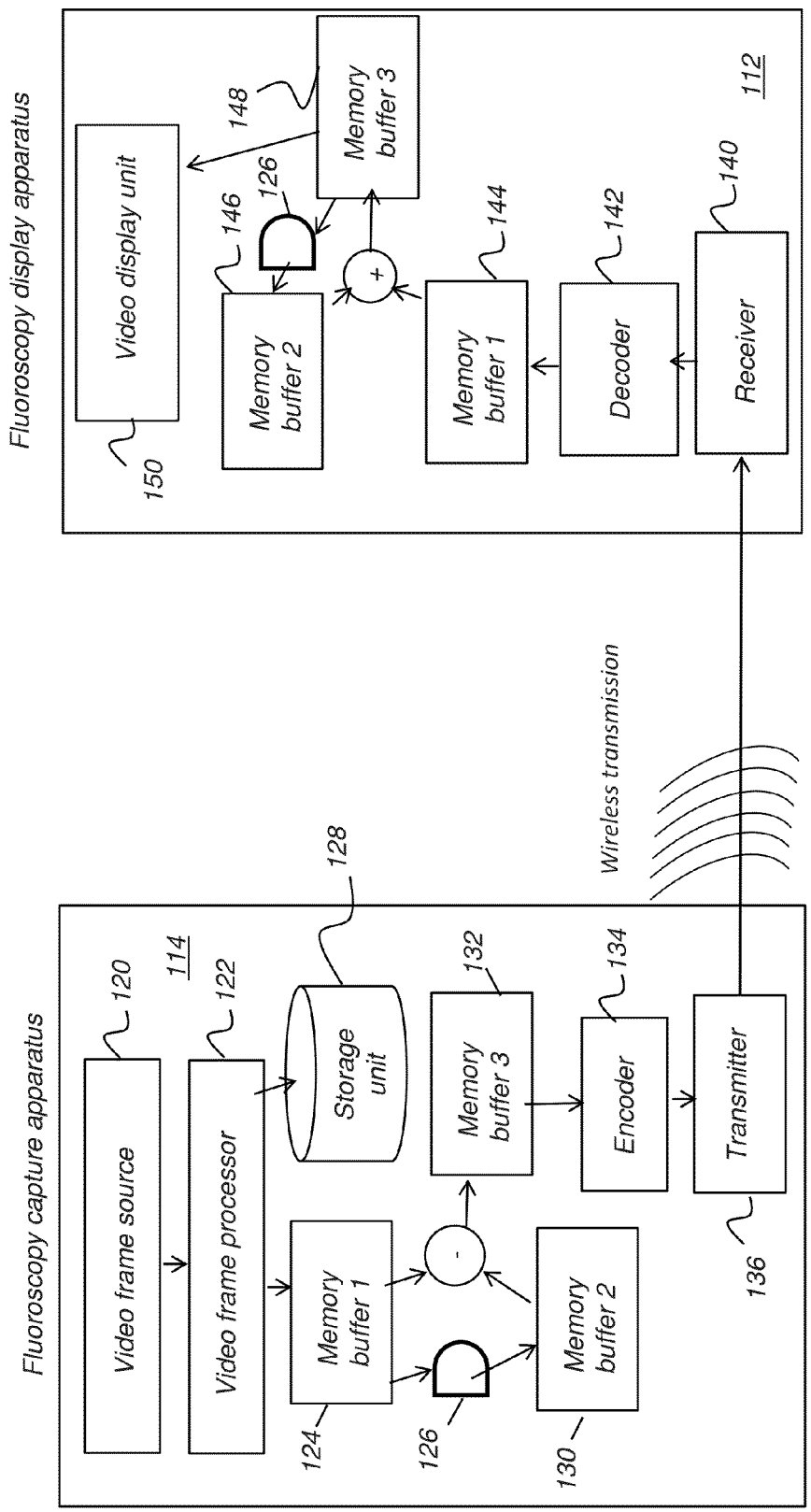
FIG. 3 is a schematic block diagram that shows functional components of a fluoroscopy capture and display apparatus according to embodiments of the present application.

One method for reducing the bulk amount of data that is transferred determines the differences between two successive frames and provides only the data that is indicative of the difference. The block diagram of FIG. 3 gives a functional overview of components for wireless transmission in the embodiment of fluoroscopy system 110 shown in FIG. 2B that uses difference information between successive image frames. At fluoroscopy capture apparatus 114, a video frame source 120 includes the DR receiver 50 components that obtain the digital data that is representative of the received radiation transmitted through patient 14 or other subject. A video frame processor 122, provided in image processing unit 58 in the FIGS. 2A and 2B embodiments, processes the received frame of image data for rendering quality and outputs the processed frame into a memory buffer 124. Utilities that can be used for improving rendering quality include, for example, tone scale adjustment, unsharp masking, and other functions. Optionally, the image data is also sent to a storage unit 128 for longer term archival. A first memory buffer 124 contains the current image frame. A second memory buffer 130 contains image content for the preceding frame. Processing compares memory buffers 124 and 130 to generate difference data between successive image frames and store this in a third memory buffer 132. The image data contents of third memory buffer 132 are then provided to an encoder 134 for compression and to a transmitter 136 for data transmission. This provides compressed fluoroscopy data for transmission to fluoroscopy display apparatus 112. For processing the next frame of image data, after a delay 126, data from memory buffer 124 becomes memory buffer 130 data.

Continuing with the sequence shown in FIG. 3, the transmitted data goes to fluoroscopy display apparatus 112. A receiver 140 receives the compressed image data and provides this data to a decoder 142. The decoded data then goes to a memory buffer 144 as a difference image. This image data is combined with image data for the previous frame that is in a memory buffer 146 to form image data that is then stored in a memory buffer 148. Image data from memory buffer 148 is then provided to a video display unit 150 for display on the display monitor and to memory buffer 146 for processing the next frame. Delay 126 is provided between transfer of data from memory buffer 148 to memory buffer 146.

With respect to the sequence described with reference to FIG. 3, it should be noted that the first image frame is handled differently, stored in the appropriate memory buffer to provide initial reference data for subsequent processing. Although described primarily with reference to the wireless embodiment of FIG. 2B, the same basic processing sequence used within capture apparatus 114 and display apparatus 112 in FIG. 3 can also be used in the hard-wired embodiment of FIG. 2A.

The difference scheme used in the sequence described with reference to FIG. 3 helps to reduce the overall amount of image data that must be transferred in wired or wireless form. Difference data can be transmitted for either or both the region of interest or the background region. However, there can still be a considerable amount of data to be transferred. Moreover, not all of the transferred data may be as important for the clinical or diagnostic function. There may be some image data for which compression is not desirable, where compression results in any loss of image content. Many types of image compression are lossy, so that some amount of image data can be compromised when compression is used. The resulting loss of data may make compression undesirable for some portion of the image content. Embodiments of the present application address this problem by allowing the viewer to define regions of interest that are of particular relevance, where loss of image content may be detrimental to the function for which fluoroscopy is being used. Image data content that lies outside this region of interest may then be subjected to some amount of lossy compression without sacrificing clinical or diagnostic value. Image data within the region of interest is then transmitted without compression, or using compression methods that are lossless.

Image data compression techniques can be lossless or lossy and embodiments of the present application can employ both types of compression for different types of image content. Lossless image data compression techniques include methods such as Run-Length Encoding (RLE) that eliminates some amount of data redundancy within a stream or sequence of data code values. Other, more sophisticated types of lossless compression for image data known to those skilled in the image processing arts include entropy coding, dictionary encoding techniques, and LZW (Lempel-Ziv-Welch) compression. File formats including JPEG (Joint Photographic Experts Group) LS, TIFF (Tagged Image File Format), GIF (Graphics Interchange Format), PNG (Portable Network Graphics), and other standard types of file formats often provide or support some measure of lossless compression encoding, with techniques and options for lossless encoding of the corresponding image data.

One general group of lossy encoding strategies known to those skilled in the image representation and storage arts uses transform coding or transform-based methods; JPEG and JPEG2000 are in this category. Another general type of encoding is bit field encoding, such as that used in BMP (BitMaP file format) encoding. Predictive encoding is yet another general type of encoding, including JPEG lossless and JPEG-LS encoding. No compression, that is, sending the data uncompressed, is also considered to provide a lossless encoding in the context of the present disclosure.

Lossy image data compression techniques can considerably reduce the amount of data for a given image but allow some loss of information, such as image content that is relatively less perceptible to the human eye. Standard image compression used with JPEG format is lossy and compresses image data by approximation techniques such as by rounding image data values where visual information is less important. Wavelet compression is another lossy compression type that can yield satisfactory results for medical images. Any type of lossy data compression or data format that compromises any of the image data is considered to provide a lossy encoding.

Figure 4B:
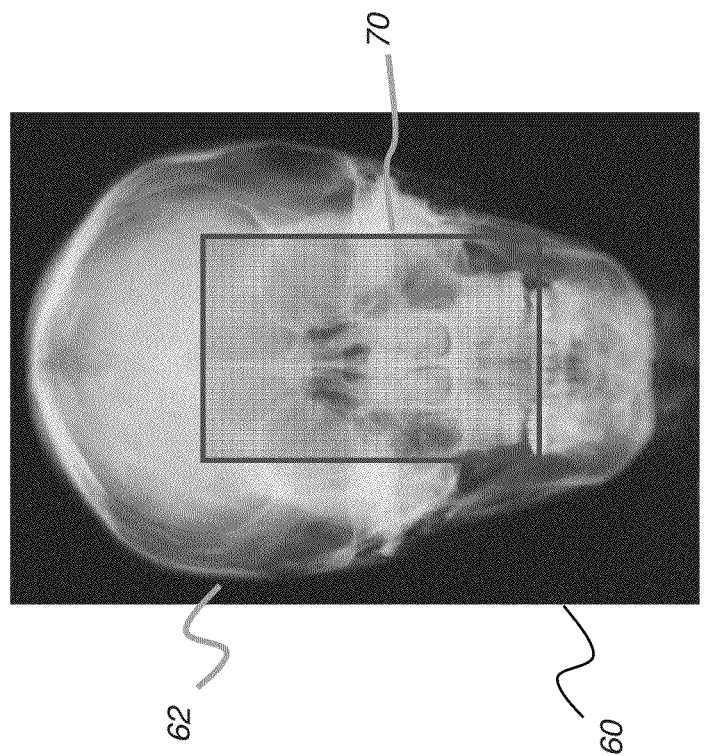
FIG. 4B is a view of the image of FIG. 4A showing a rectangular region of interest, defined according to an embodiment of the present application.
Figure 4A:
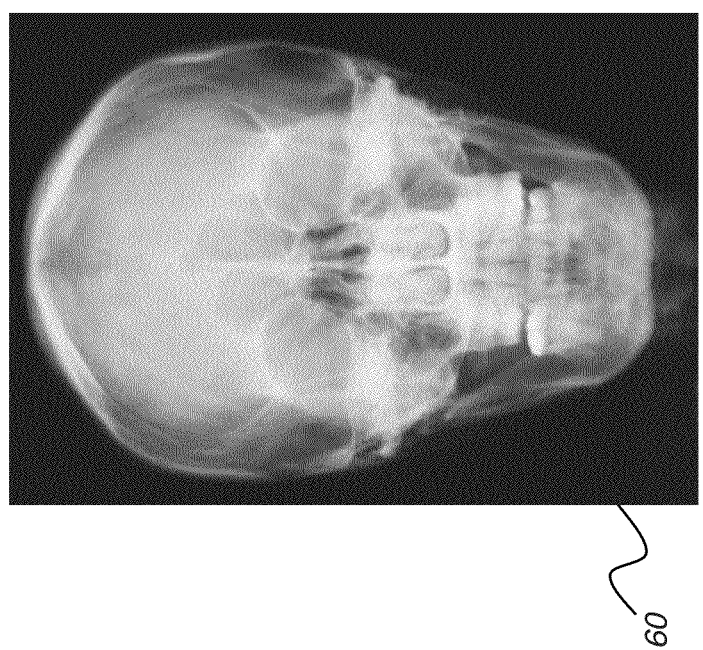
FIG. 4A is a plan view that shows a fluoroscopy image of a patient's head.

FIG. 4A shows a fluoroscopy image 60 that includes a patient's head. For a particular procedure, only a portion of the patient's head is of interest. As shown in FIG. 4B, there is a region of interest (ROI) 70, identified as a rectangular area in this example. The balance of image 60, exclusive of region of interest 70, is a background region 62.

Figure 5:
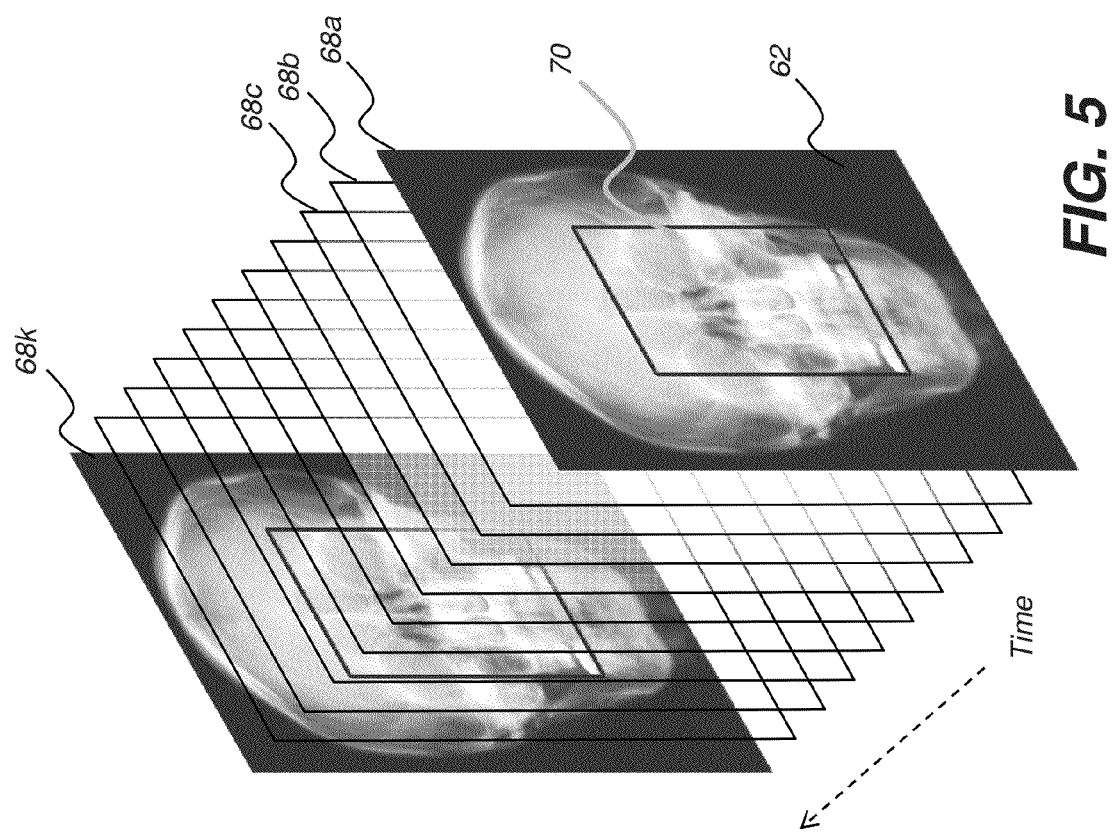
FIG. 5 is a diagram that shows successive image frames in a fluoroscopy imaging sequence.

FIG. 5 shows a series of successive image frames 68a, 68b, 68c . . . 68k in a small portion of an example fluoroscopy sequence. As can be seen, the same anatomy is imaged in each image frame. Of primary interest to the practitioner is region of interest 70 within each frame; background region 62 is of less value for the procedure that is being performed. For this reason, embodiments of the present application allow different types of image processing and image data compression and transmission for the two portions of the image, that is, for region of interest 70 and background region 62.

Regardless of the method that is employed for image compression and transmission, region of interest 70 must first be identified, relative to the image area of the digital detector or receiver, DR receiver 50 (FIGS. 2A, 2B). This can be done in a number of ways, such as those shown in the examples of FIGS. 6A through 6D.

Figure 6A:
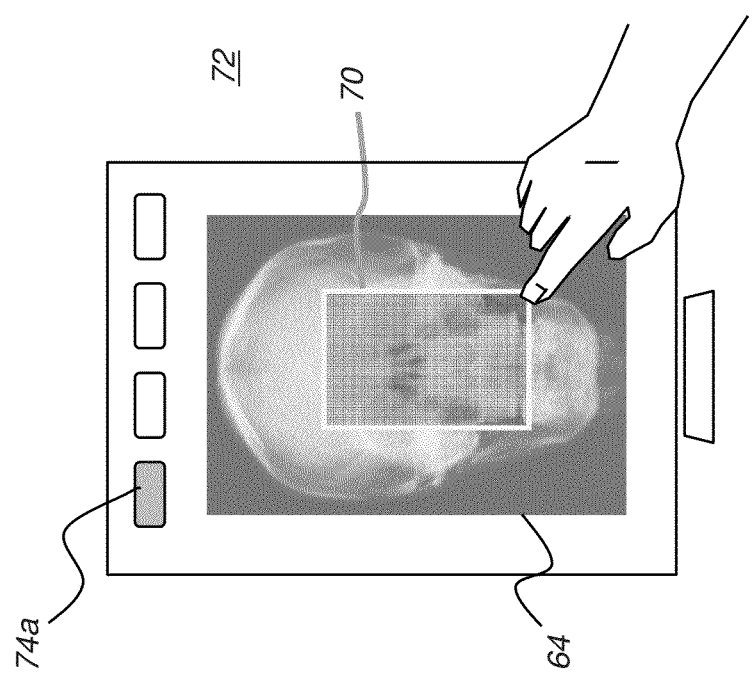
FIG. 6A is a view of an operator interface for defining the region of interest for a fluoroscopy imaging sequence using a rectangle.
Figure 6B:
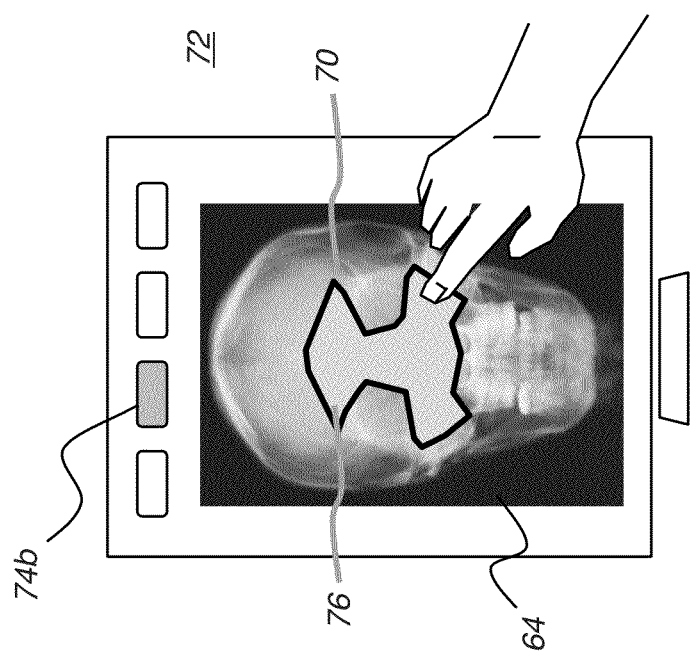
FIG. 6B is a view of an operator interface for defining the region of interest for a fluoroscopy imaging sequence using a mask.

Some type of viewer instruction or action is used to define the region of interest. FIGS. 6A and 6B show identifying region of interest 70 according to a viewer instruction entered on the operator interface, termed a Graphical User Interface (GUI) 72 on display monitor 44 (FIGS. 2A, 2B). In FIG. 6A, a touch screen interface allows the viewer to outline region of interest 70 directly on a displayed basis image 64. Basis image 64 is a single fluoroscopy image that is optionally obtained as a part of initial setup for the fluoroscopy session. An optional control button 74a enters an operator instruction that enables rectangular outlining, or outlining using a circle or other appropriate geometric shape, onto the displayed basis image. In the example shown, the operator uses conventional interface actions to identify diagonal corners of a rectangle that defines region of interest 70 on basis image 64.

Given viewer entered instructions that identify the ROI, the imaging system then correlates the defined ROI with the corresponding image area of the digital radiography receiver. The use of a basis image is optional; various methods could be used to isolate ROI 70 from the balance of image 60 and to provide a mapping that relates one or more areas of the digital receiver to the ROI.

FIG. 6B shows definition of region of interest 70 using a mask 76 that is identified or defined by the user with reference to the basis image. Mask 76 may be selected from a series of standard masks, or may be edited or drawn free-form using a touch screen or other type of screen pointer that indicates points, basic shapes, or areas of the image. An operator instruction at a control button 74b specifies this function.

User tracing or placement of a shape that defines a region of interest relative to a basis image can be performed in a number of ways, using standard user interface tools and utilities, that include a touch screen or use of a computer mouse or stylus or other pointer. According to an alternate embodiment of the present application, an explicit user instruction that is entered with respect to a basis image is not needed for ROI identification. Instead, a default region of interest 70 is automatically assigned within the image, such as that portion of the image area centered in the middle of the display screen, for example. Utilities are then provided for performing functions such as panning or positional adjustment, sizing and scaling and other functions that may further define the region of interest according to viewer instruction.

The viewer instruction can thus identify specific points that define the region of interest or can instruct the system to utilize a default image area or a selected one of a set of default image areas for defining the region of interest.

Figure 6C:
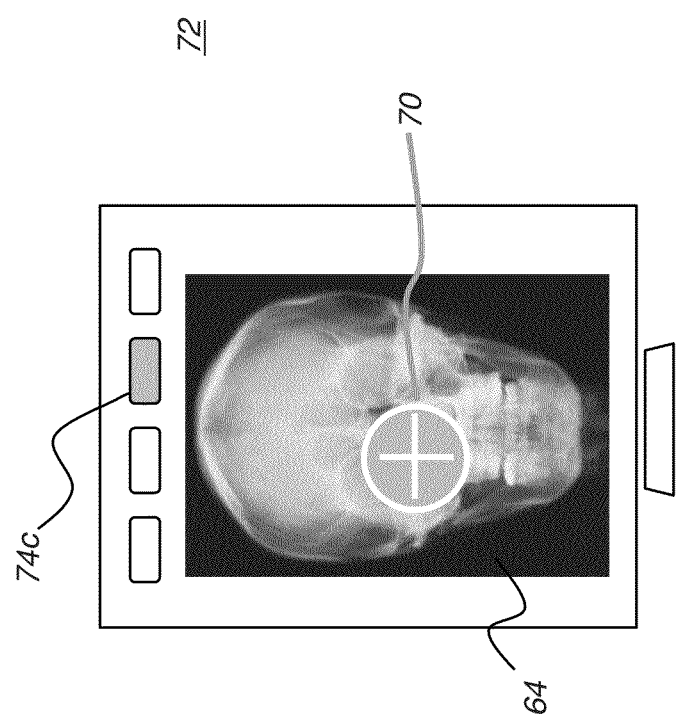
FIG. 6C is a view of an operator interface for defining the region of interest for a fluoroscopy imaging sequence using a device or object.

The example of FIG. 6C shows another default arrangement that can be used. A viewer instruction entered on a control button 74c instructs the system to track a device or object, such as an instrument, camera, probe, needle, tube, or other object that is placed on or inserted into the patient anatomy being imaged. Region of interest 70 is then defined in the vicinity of the tracked device or object and can have a default size, such as a given diameter about the object or device, or a viewer-defined size. For tracking an object, an initial calibration or setup procedure may be required for identifying the object and defining the size of the corresponding region of interest within which the object is centered.

Figure 6D:
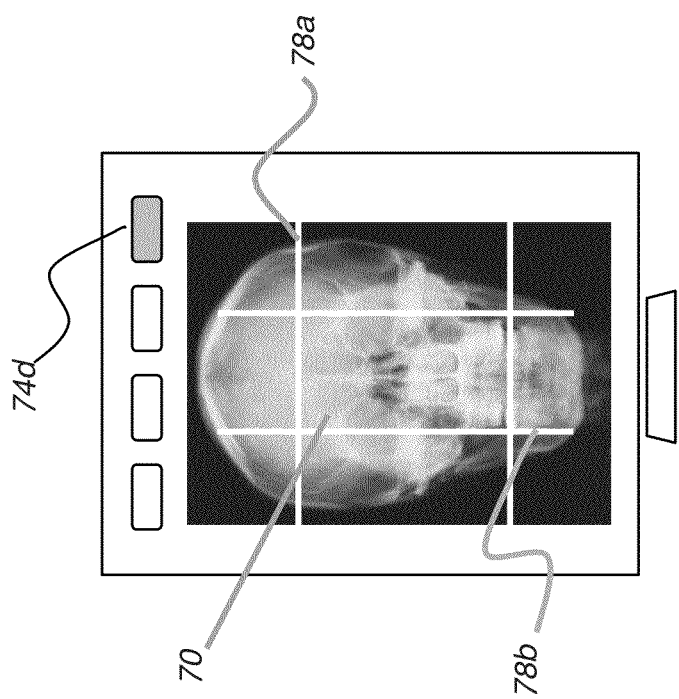
FIG. 6D is a view of an operator interface for defining the region of interest for a fluoroscopy imaging sequence using a collimator setting.

The example of FIG. 6D shows another alternate embodiment in which the operator instruction, entered using a control button 74d, tells the system to define the boundaries of region of interest 70 according to the settings of collimator 22 blades (FIGS. 2A, 2B), as adjusted by the viewer. Collimator 22 typically provides either a circular region of variable diameter or a rectangular area of variable dimensions. In the example of FIG. 6D, a rectangular embodiment is shown. Lines 78a and 78b show the collimator blade settings, effectively providing a rectangular area as region of interest 70. On some systems, collimator blades are motor controlled, allowing the viewer to adjust and view settings for the area of interest as part of the overall equipment setup. According to an alternate embodiment of the present application, the operator can adjust collimator blade positions and observe blade repositioning directly on the display screen, allowing the system to adopt and change ROI boundaries according to blade settings. To obtain suitable coordinates for ROI identification, the imaging system detects the positions of collimator blades, then translates this positional information into corresponding coordinates on the detector for ROI identification.

Thus, in any of a number of ways, an ROI is identified, wherein the ROI maps to, or relates to, the image area of the digital detector of the imaging system. The viewer instruction that identifies the ROI may be explicitly entered using the basis image as described earlier, or may be inferred from a collimator or other adjustment. Alternately, the viewer instruction may simply be a command or instruction to prepare for obtaining images, thus prompting the imaging system to use a default ROI definition based on the type of image being obtained or based on sensed settings of the collimator, for example.

Once region of interest 70 is defined on the basis image, the viewer can enter an explicit instruction that indicates completion of this process. Alternately, the given settings are used automatically and exposure can begin. The specified region of interest settings are maintained until specifically adjusted by the viewer.

Figure 7:
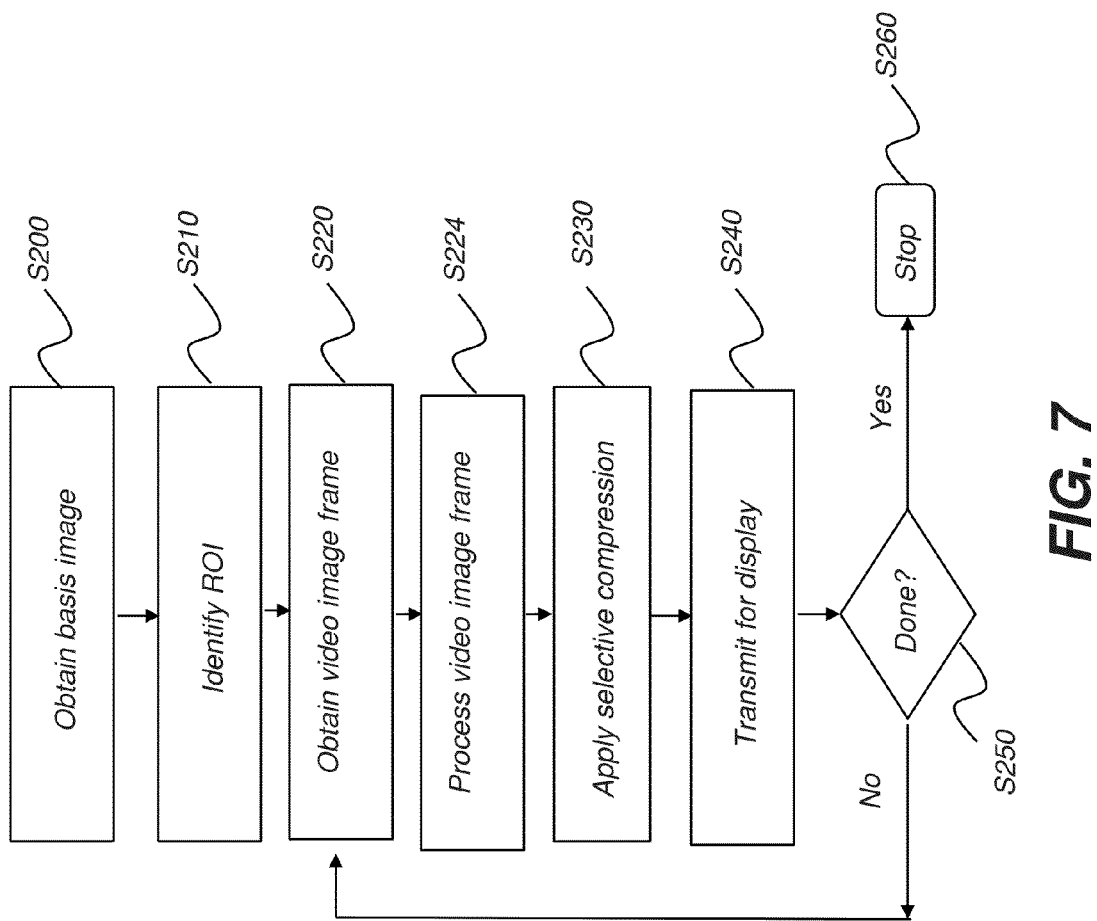
FIG. 7 is a logic flow diagram that shows steps for applying a selective compression sequence according to an embodiment of the present application.

The logic flow diagram of FIG. 7 shows steps for fluoroscopic imaging according to an embodiment of the present application. An optional obtain image step S200 obtains the basis image that is used for region of interest identification in some embodiments of the present application. In an identify ROI step S210, the region of interest is identified, such as using procedures described with respect to FIGS. 6A through 6D. As noted previously, the ROI may be defined by default, without explicit operator markup on a basis image. The ROI may be automatically defined by default upon entry of an operator instruction to acquire a particular image.

Continuing with the FIG. 7 sequence, imaging proceeds with obtain video frame step S220, in which a frame of image data is acquired. The acquired image data is then processed in a processing step S224. Following image data processing, a selective compression step S230 then applies lossy compression to the background region pixels. Lossless compression (including no compression, where this feature is used) is similarly applied to region of interest pixels. A transmission step S240 then transmits the encoded, processed image data to fluoroscopy display apparatus 102, 112 (FIGS. 2A, 2B). A termination test S250 then either proceeds if another frame is needed or moves to a termination step S260 to end the fluoroscopic imaging session.

Using the sequence described with reference to FIG. 7, the fluoroscopy system can selectively compress image data that is of less interest to the viewer, while providing no compression to data within the region of interest. According to an alternate embodiment of the present application, two different compression levels are used. An aggressive, lossy compression is used for background region 62 content. A slightly lossy compression algorithm, allowing relatively less loss of image content by comparison with that applied for background region 62, is then used for region of interest 70. An algorithm is considered to be more or less lossy than another algorithm based on a measure of how much of the original processed image data is lost or modified when the compressed data is decompressed.

Figure 8A:
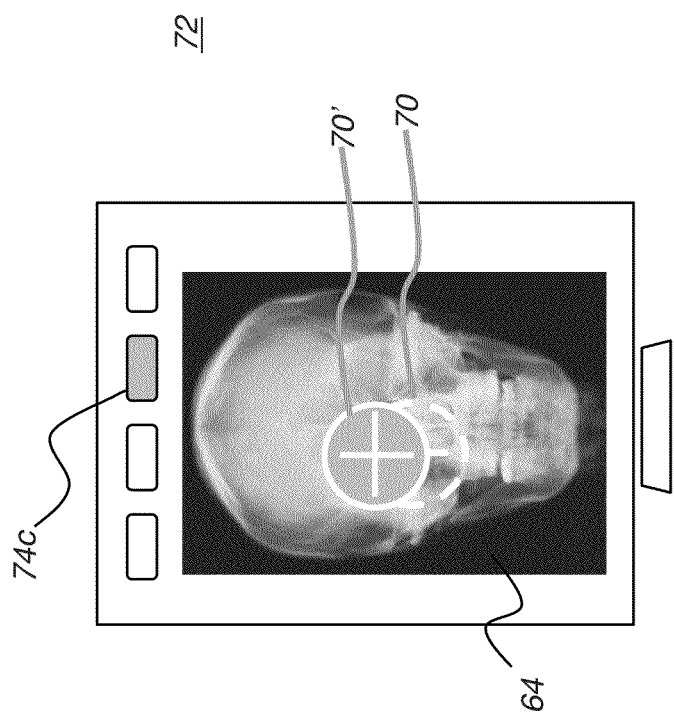
FIG. 8A is a view of a display screen showing a shift in position of the region of interest according to movement of an object or device.

According to an embodiment of the present application, region of interest 70 can be shifted in position after it has been initially defined, during the fluoroscopy session. Referring to the example of FIG. 8A, a probe (not visible in the figure) is tracked and region of interest 70 is centered on the end of the probe, as indicated by crosshairs in FIG. 8A. Changing of probe position is tracked. As the probe is moved (upward in the example of FIG. 8A), a shifted region of interest 70' is defined accordingly.

Figure 8B:
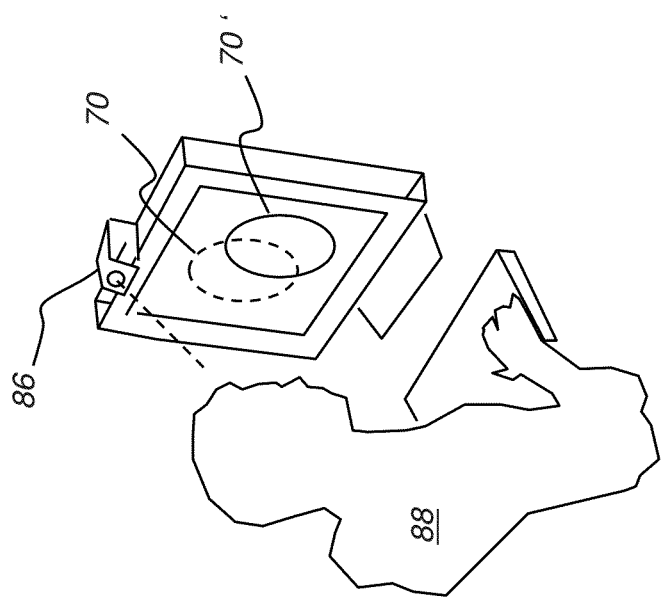
FIG. 8B is a view of a display screen showing a shift in position of the region of interest according to a change in operator focus of attention.

According to an alternate embodiment of the present application, as shown in FIG. 8B, region of interest 70 can be shifted according to a gesture or other indication from a viewer 88. A gaze tracking mechanism is provided, observing viewer 88 attention using a camera 86 and signaling changes in viewing focus. As viewer 88 attention moves toward a different part of the image, region of interest 70 shifts to provide a shifted region of interest 70'.

Figure 9A:
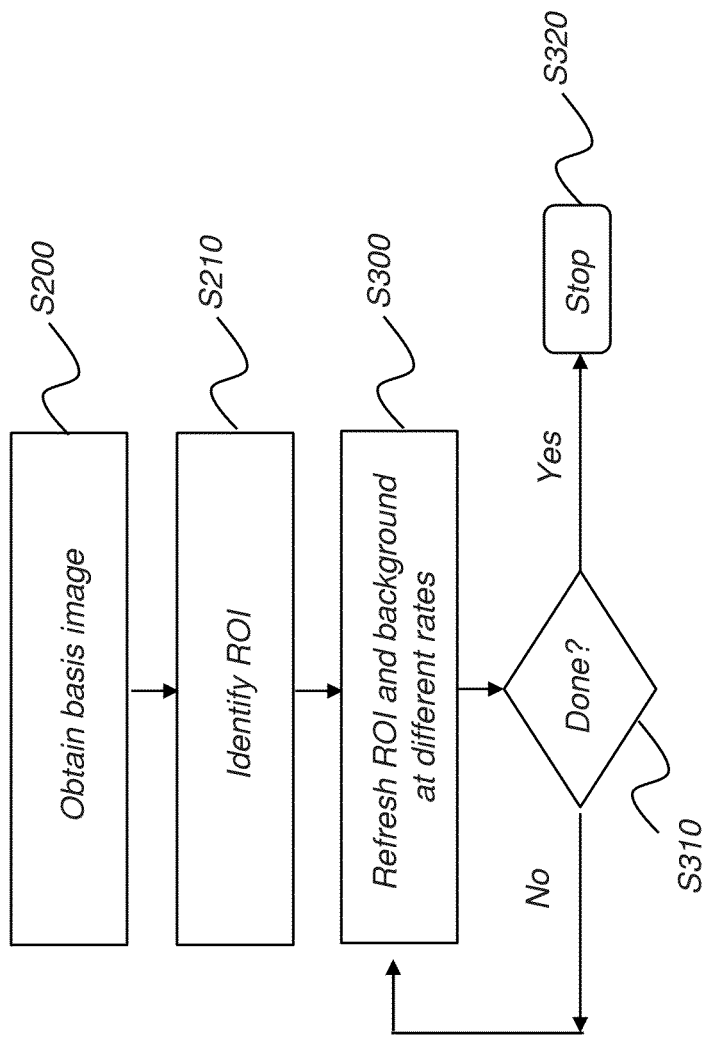
FIG. 9A is a logic flow diagram that shows steps for transmitting image data from region of interest and background portions of an image at different rates.
Figure 9B:
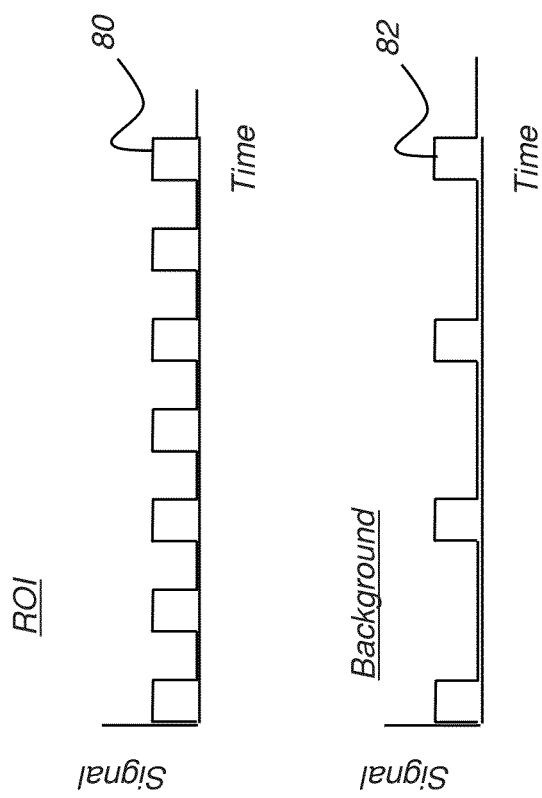
FIG. 9B shows timing diagrams for transmitting image data from region of interest and background portions of an image at different rates, as described with reference to FIG. 9A.

A different type of image data compression can be provided by effectively adjusting the timing of image update for the region of interest 70 so that its data refresh is more frequent than the update for background region 62. The logic flow diagram of FIG. 9A shows a sequence of steps for fluoroscopy imaging using this alternate technique. Optional obtain image step S200 and Identify ROI step S210 are the same as described earlier with reference to FIG. 7, allowing the viewer to define the region of interest that requires better resolution than background content, or assigning the region of interest by default, as previously described. A refresh step S300 provides a transmission sequence that refreshes the region of interest at a higher (faster) rate than it refreshes background content. FIG. 9B shows timing diagrams 80 and 82 that compare the refresh rates for region of interest 70 content and background region 62 content, respectively. By refreshing region of interest 70 content more often, the overall volume of image data that must be transmitted is significantly reduced, without significant impact on the quality of the displayed fluoroscopic image. Continuing with the sequence of FIG. 9A, a termination test S310 then either proceeds if another frame is needed or moves to a termination step S320 to end the fluoroscopic imaging session.

It should be noted that once the region of interest is identified, the corresponding data content is handled appropriately for fluoroscopy display apparatus 102 (FIG. 2A) or 112 (FIG. 2B) at host processor 52. For a line of pixels, for example, one or more portions of the pixels may be part of the region of interest; other pixels in a line of pixels may be part of the background content. Pixel mapping to handle the different compression types can be relatively straightforward for the rectangular ROI 70 of FIG. 6A. For mask 76 of FIG. 6B, a binary mask is generated and provided to host processor 52, allowing the pixel data that is mapped to ROI and background content to be readily identified and appropriately handled for display.

According to an embodiment of the present application, different tone scales can be applied to the ROI and background content. This type of conditioning helps to visually differentiate background from ROI content for the viewer. Other types of perceptible image treatment can be provided over the full background or ROI areas, including use of different contrast or brightness levels, filtering, or use of color, for example.

According to an alternate embodiment of the present application, multiple levels of compression are used, depending on factors such as proximity to the region of interest. Displayed background content nearest the region of interest undergoes only slight compression, while content furthest from the region of interest is highly compressed.

In general, the image data content for fluoroscopic viewing is optimized for presentation, rather than for processing. This type of treatment can relate to how images are stored and processed in DICOM (Digital Imaging and Communications in Medicine) imaging apparatus.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for displaying a sequence of fluoroscopic images of a patient, comprising:
   defining, within the image area of a digital image receiver, in response to one or more viewer instructions, a region of interest and a background region disposed outside the defined region of interest;
   obtaining a succession of fluoroscopic images at a digital image receiver and, for image pixels within each of the succession of images:
   (i) encoding and transmitting background region pixels to a display apparatus using a lossy encoding, with transmission at a first refresh rate, wherein more than one type of lossy encoding is used for the background region pixels, according to distance from the region of interest; and
   (ii) transmitting region of interest pixels to the display apparatus using a second encoding, with transmission at a second refresh rate that is higher than the first refresh rate; and
   displaying the succession of fluoroscopic images on the display apparatus.

2. The method of claim 1 wherein the pixel data is transmitted wirelessly.

3. The method of claim 1 wherein the one or more viewer instructions are entered using a mouse or other pointer.

4. The method of claim 1 wherein the one or more viewer instructions are entered using a touch screen.

5. The method of claim 1 wherein the one or more viewer instructions define a rectangular region of interest.

6. The method of claim 1 wherein the one or more viewer instructions define a non-rectangular region of interest.

7. The method of claim 1 wherein the one or more viewer instructions comprise operator actions for setting up or initiating an exposure.

8. The method of claim 1 wherein the more than one type of lossy encoding includes transform-based encoding.

9. The method of claim 1 wherein the more than one type of lossy encoding includes bit field encoding.

10. The method of claim 1 wherein the more than one type of lossy encoding includes predictive encoding.

11. The method of claim 1 wherein displaying the succession of fluoroscopic images comprises displaying the region of interest and background region with different image contrast, brightness level, tone scale, filtering, or color.

12. The method of claim 1 wherein the one or more viewer instructions indicate use of an object to define the region of interest.

13. The method of claim 1 further comprising shifting the position of the region of interest according to operator gaze.

14. The method of claim 1 further comprising shifting the position of the region of interest according to movement of an object.

15. The method of claim 1 wherein a portion of the pixel data for either or both the background region and the region of interest is transmitted as difference data between successive image frames.

16. The method of claim 1 wherein the second encoding is lossless.

17. The method of claim 1 wherein the second encoding is less lossy than the lossy encoding used for background pixels.

* * * * *